United States Patent [19]  
Garner et al.

[11] 4,419,451  
[45] Dec. 6, 1983

[54] OXYGEN SCAVENGING SYSTEM FOR ANAEROBIOSIS

[75] Inventors: Richard L. Garner; Luther Winans, Jr., both of Abilene, Tex.

[73] Assignee: Becton Dickinson and Company, Paramus, N.J.

[21] Appl. No.: 265,875

[22] Filed: May 21, 1981

[51] Int. Cl.$^3$ .......................... C12M 1/22; C09K 3/00; C01B 3/08; C01B 15/16

[52] U.S. Cl. ............................ 435/298; 252/188.25; 422/211; 422/222; 422/305; 423/657; 435/801

[58] Field of Search .............. 435/296, 297, 298, 300, 435/301, 801; 422/211, 222, 305; 252/188.25; 423/657

[56] References Cited

U.S. PATENT DOCUMENTS

| | | | |
|---|---|---|---|
| 3,073,750 | 1/1963 | Greenblatt | 435/298 |
| 3,483,089 | 12/1969 | Brewer | 435/801 X |
| 3,728,228 | 4/1973 | Duranty | 435/298 X |
| 3,986,935 | 10/1976 | Jackson, Jr. et al. | |
| 4,038,148 | 7/1977 | Miller et al. | 435/801 X |
| 4,038,149 | 7/1977 | Liner et al. | 435/298 X |
| 4,064,226 | 12/1977 | Becker et al. | 423/657 |
| 4,108,728 | 8/1978 | Spinner et al. | 435/296 |
| 4,200,610 | 4/1980 | Swaine et al. | 435/801 X |
| 4,287,306 | 9/1981 | Brewer | 435/801 X |
| 4,342,738 | 8/1982 | Burgund | 423/657 |

Primary Examiner—Robert J. Warden

[57] ABSTRACT

A self-contained system is provided for producing an oxygen-free environment for anaerobiosis and culturing wherein the system possesses the ability to provide and maintain the oxygen-free environment, even after the opening and closing of the sealed container therefore several times. The system includes a metallic couple, preferably copper-magnesium, which reacts with water to induce and maintain the oxygen-free environment. The degree of addition of water to the system controls the rate of reduction of the environment. The system possesses a dual oxygen scavenging function by the controlled addition of water. That is, if a small amount of moisture is added to the system couple of the invention, hydrogen is liberated, which causes a drying in the system simultaneously with a reaction of a portion of the couple to gradually scavenge oxygen from the environment, simultaneously with the liberation of hydrogen. If desired, in such an arrangement, the subsequent addition of water generates hydrogen again until all the magnesium is used up, in order to provide a subsequent oxygen scavenging property. In addition, the system includes a sealable petri dish so conformed to include means for maintaining the system of the invention in combination with an indicator for anaerobiosis, a catalyst for the system, a carbon dioxide generator, and space for the culture media.

24 Claims, 7 Drawing Figures

OXYGEN SCAVENGING SYSTEM FOR ANAEROBIOSIS

BACKGROUND AND STATEMENT OF THE INVENTION

Generally speaking, this invention relates to a system for establishing and maintaining an oxygen-free environment. More particularly, this invention relates to such a system which will establish such an oxygen-free environment in any sealed container, and which will regenerate such an environment subsequently on a repetitious basis when the container is unsealed for inspection and then resealed. As such, the system is a self-contained arrangement which has the ability not only to establish an anaerobic environment, but also to maintain and/or re-establish such an environment.

As will be appreciated, in the culturing of various media, it becomes important to inspect the state of the culture at various stages. In doing so, it becomes necessary to open the container in which the media is contained for such inspections, particularly when an anaerobic jar is utilized wherein several petri dishes are arranged or stacked. When the sealed container is opened, under those circumstances, it becomes necessary to re-establish the oxygen-free environment when the container is re-closed. This involves the utilization of additional catalysts and the insertion of an entirely new anaerobic generating system in order to re-establish the oxygen-free environment. Not only that, but all of the cultures are exposed and disturbed when the jar is opened, even though only one or two may need inspection at that time.

With this invention, by contrast, an arrangement is provided for re-establishing the oxygen-free environment over several repeated openings automatically with the resealing or reclosure of the container in which the culture media is contained. As such, separate small petri dishes, for example, may be utilized for the system of the invention here wherein each individual petri dish has self-contained therein a system for generating an oxygen-free environment which re-establishes itself automatically with reclosure of the container. Alternatively, when the couple is only moistened, the metal of the couple first liberates hydrogen which dries the environment and causes a continuous reaction with any free oxygen in the sealed environment. Thus, there is a continuous scavenging function when moisture is added in only a small quantity to the couple of the invention here. Thereafter, with the addition of water, the process is repeated with the generation of hydrogen at a moderate rate until all of the metal is used up.

Thus, this system, in accordance herewith, has a double action as an oxygen "scavenger." By placing approximately one and a half grams of the metallic couple inside a conventional petri dish or plate, for example, and exposing to water, either by high humidity as in pouring fresh molten culture media such as agar into the plate, or by direct addition of water to the couple, hydrogen is released to react with the free oxygen in the presence of a catalyst, also inserted into the container. This removes the free oxygen present in the environment. After this reaction has stopped, the dried metallic couple left will slowly react directly with any free oxygen left, and/or diffused out of the culture medium forming a metallic oxide, thus helping to maintain the environment in its reduced state. The formed metallic oxide will further dry the environment.

As will be appreciated by practitioners-in-the-art, each sealed environment, in accordance with the system herein, such as a petri dish or plate, will contain the metallic couple together with a catalyst such as palladium supported upon alumina, and an indicator for determining anaerobiosis. In addition, the container may include a carbon dioxide tablet for generating carbon dioxide. The indicator for indicating anaerobiosis may be methylene blue, indigo carmine or resazurin.

As discussed above, anaerobic petri plates or dishes may be opened, examined and then closed several times, and on each occasion, the plate will return to its reduced state with the addition of a small quantity of water. Thus, each plate automatically returns to its reduced state and maintains its environment during handling and observation.

Representative metals which may be utilized for carrying out this invention include magnesium, strontium and metallic calcium. Beryllium and barium may be used, but are extremely poisonous. Preferably, metallic magnesium is used in the form of magnesium turnings. The metallic salt added to the metal to form the metallic couple may be, for example, copper, platinum, palladium, tin, iron, nickel or cobalt. Preferably, it is a copper salt, and most preferably copper chloride. The catalyst for generating the anaerobiosis from this metallic couple may be, for example, a supported palladium or a supported platinum. However, it is within the purview of this invention that the metallic couple of the system herein may act as its own catalyst. If a metallic couple is formed from palladium and magnesium, for example, this combination may act as its own catalytic generating agent. Other salts which combine to act as their own catalytic generating agents include nickel, platinum and cobalt.

In forming the metallic couple of the system of the invention, a weak solution of cupric chloride may be provided which is poured through a funnel and over a portion of magnesium turnings. The coupling must be carried out rapidly in order to bring about completion of the reaction as soon as possible. In forming an anaerobic generating sealed container system, in accordance herewith, the quantity of copper-magnesium couple, for example, will be selected according to the volume of the container in which it is to be placed. For example, 0.5 grams of a copper-magnesium couple establishes a complete oxygen-free environment in a volume of 40 cc in about 2 hours. Anaerobic jars with a volume of 2.2 liters, for example, require 2 grams of a magnesium-copper couple in order to establish an aerobic atmosphere in a useful period of time for most culturing applications. The metallic couple system of the invention here is so effective, for example, that it will operate to establish anaerobiosis without a catalyst. The problem with operating under these conditions is that the reaction is too slow and will not be effective for certain very sensitive cultures.

Representative chemical reactions established for maintaining anaerobiosis in accordance herewith and assuming a copper-magnesium couple is being utilized, are as follows:

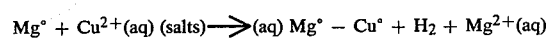

$Mg° + Cu^{2+}(aq)\ (salts) \longrightarrow (aq)\ Mg° - Cu° + H_2 + Mg^{2+}(aq)$ -continued

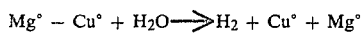

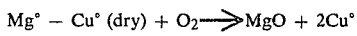

Thus, the invention here provides a self-contained petri dish or other sealed container containing an anaerobic environment and/or reduced media, with each petri dish being clearly visible and easily handled so that one or many such dishes may be run simultaneously without the need of a large bulky system such as anaerobic jars or anaerobic incubators, for example. Each petri dish may be handled separately without disturbing any other ones of the dishes being run while observing the one. The system of the invention provides a dual action system for removing oxygen in that first hydrogen is generated which catalytically reacts with oxygen present for establishing anaerobiosis, and secondly by combining directly with oxygen to form a metallic oxide. Each single anaerobic plate or dish, furthermore, has the ability to work several times, thus automatically generating hydrogen which is catalytically oxidized to water which allows the dish to be streaked, opened, closed, and opened repeatedly several times, with the re-establishment of the anaerobiosis. Moreover, because the couple in its moist or semi-dry state reacts slowly with oxygen which may be still present in the container, such a property serves to remove traces of residual oxygen from the medium and to maintain a reduced environment.

It will be appreciated, because of the relatively small space of individual sealed containers, and the capability of multiple openings, the exposure time to ambient is cut to a minimum with the re-estabishment of anaerobiosis within only several minutes. Because of this, clinical cultures can be taken, streaked immediately and taken to the laboratory so as to increase isolation efficiency and decrease the time lag between taking clinical specimens and the diagnosis and sensitivity results thereof.

As illustrative of procedures for formulating metallic couples for use in systems, in accordance with this invention, one may note the following examples. It is to be understood, however, that these examples are being presented with the understanding that they have no limiting character on their broad disclosure of the invention as generally set forth herein and as directed to men skilled in the art.

EXAMPLE 1

In this example, magnesium metal was used in the form of turnings. 2.13 grams of magnesium metal turnings were utilized and 50 grams of cupric chloride solution was poured over the powder. A tris buffer was utilized to enhance the reaction, although it has been found that buffers are not really required for carrying out the reaction here. The buffer is tris-hydroxymethyl aminomethane. The quantity of tris buffer used was 0.06 grams. The reaction was allowed to occur for about 30 seconds. Thereafter, the reactants were washed with 30 milliliters of distilled water in four separate quantities, and then the reaction product was washed four times with acetone. The material was then air dried to flowing and a final weight of dried material of 2.33 grams was obtained. To this material, a powdered palladium catalyst was added in the quantity of 0.66 grams. This material was added to a jar with a methylene blue indicator and 7 milliliters of distilled water was added and the jar sealed. The pressure indicator on the jar indicated a generated pressure of 2.8 pounds per square inch (psi). A large amount of water condensate formed on the sides of the jar. The indicator turned white indicating anaerbiosis. The results of the run are as follows:

| TIME | % $O_2$ |
| --- | --- |
| 0 Minutes | 21.00 |
| 5 Minutes | 20.00 |
| 10 Minutes | 18.00 |
| 15 Minutes | 15.00 |
| 20 Minutes | 11.00 |
| 30 Minutes | 3.00 |
| 40 Minutes | 2.00 |
| 50 Minutes | 1.00 |
| 60 Minutes | 0.70 |
| 70 Minutes | 0.50 |
| 80 Minutes | 0.30 |
| 90 Minutes | 0.10 |

Thus, in only one hour the oxygen percentage in the jar was reduced from 21% to 0.70%, and was reduced to 0.10% in ninety minutes.

EXAMPLE 2

In this example, magnesium powder was used in the quantity of 10.03 grams. Cupric chloride in the amount of 2.52 grams was used, together with 0.20 grams of sodium chloride, and 0.20 grams of tris buffer. 61.40 milliliters of water were used to wash the reactants four times, followed by acetone washing four times. The resulting material was air dried to a total weight of 13.80 grams.

The resulting material may be formed into tablets in a tablet die and stored in an air-tight container. The mixture for formulating the tablets includes, for example, one gram of sodium chloride and 0.41 grams of tris buffer added to 2.03 grams of treated magnesium powder of Example 2. The tablets formulated in this manner are a more convenient form for use in individual petri dishes, such as those disclosed herein.

As further illustrative of the invention herein, one may note the accompanying drawings illustrating a form of petri dish which may be utilized in the system of the invention, in accordance herewith.

DETAILED DESCRIPTION OF THE INVENTION

Figure 1:
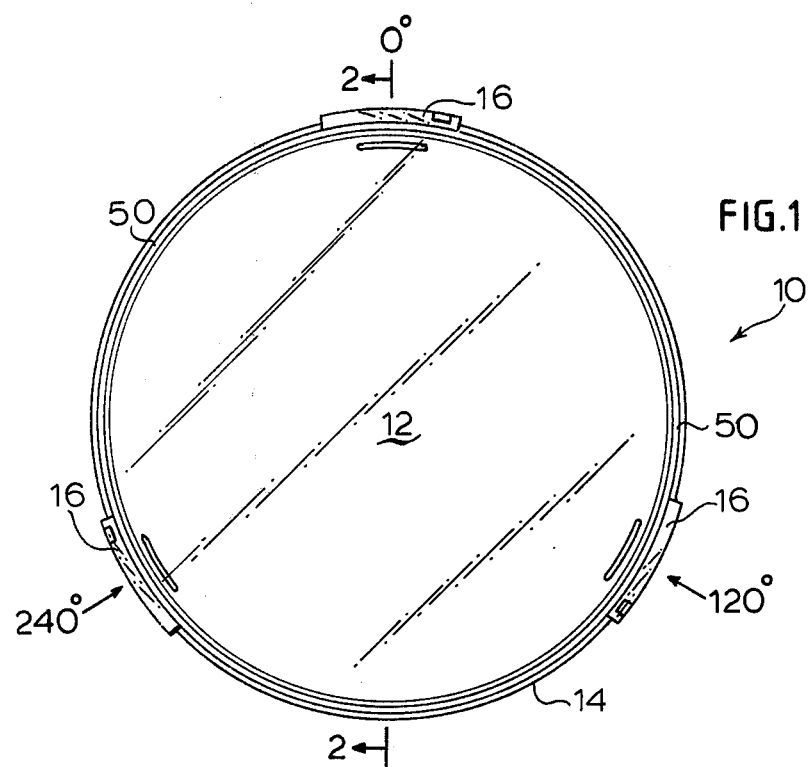
FIG. 1 is a top plan view of the bottom portion of the sealable petri dish of the invention.
Figure 2:
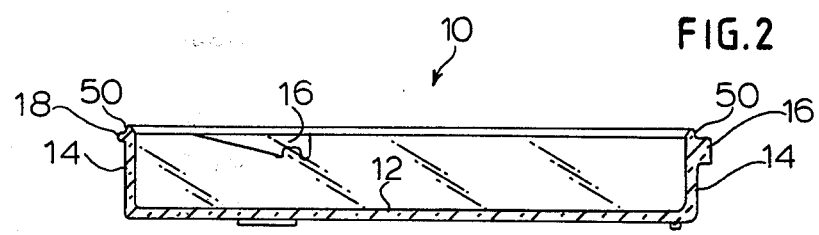
FIG. 2 is a sectional view taken along lines 2—2 of FIG. 1.

Referring to the drawings in which like reference characters refer to like parts throughout the several views thereof, FIG. 1 shows a bottom part 10 of a sealable petri dish forming a portion of the system, in accordance herewith, with the bottom part 10 having bottom wall 12 and an annular upstanding wall 14. Spaced circumferentially along walls 14 are a plurality of locking connections 16 forming one-half of a plurality of bayonet type sliding lock connections for maintaining a sealed connection between bottom part 10 and related top part 20, shown in FIG. 3. As shown in FIG. 2, bottom part 10 includes an annular abutment 18 which serves to form an annular platform for receiving the bottom edge 52 of the top of the annular wall 24 of top part 20. The upper edge of the wall 24 of top part 20 includes an annular flange 29 which is received on the abutment 18 of bottom part 10.

Figure 3:
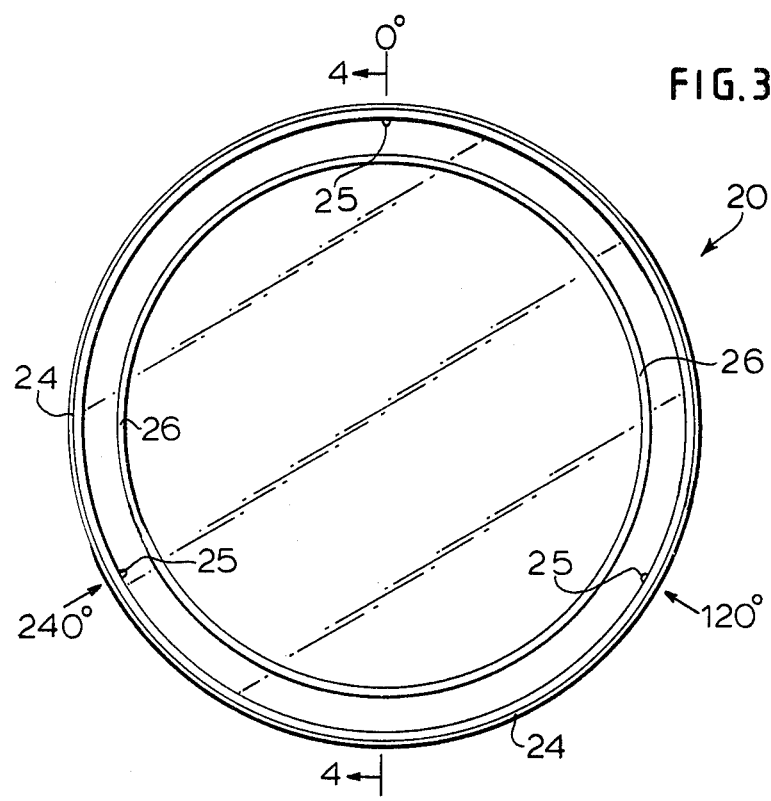
FIG. 3 is a bottom plan view of the top portion of the sealable petri dish of FIG. 1.
Figure 4:
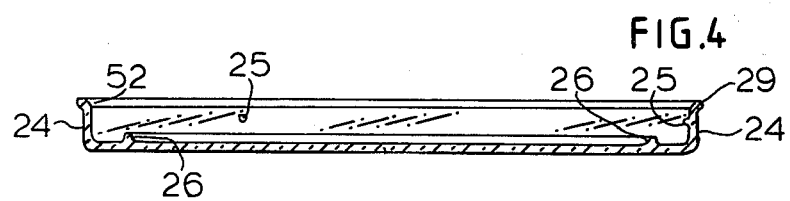
FIG. 4 is a sectional view taken along lines 4—4 of FIG. 3.

As shown in FIG. 3, top part 20 includes a plurality of spaced apart locking abutments 25 which cooperate with the bayonet connections 16 of bottom part 10 for maintaining a locked sealable connection between the top part 20 and the bottom part 10 in the closed position of the sealable petri dish, in accordance herewith.

Figure 6:
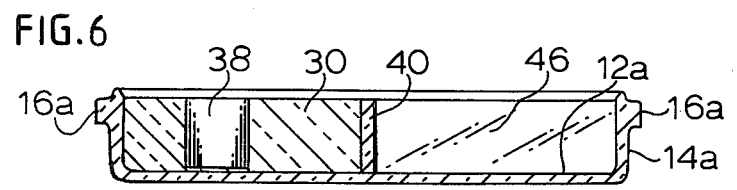
FIG. 6 is a sectional view taken along lines 6—6 of FIG. 5.
Figure 5:
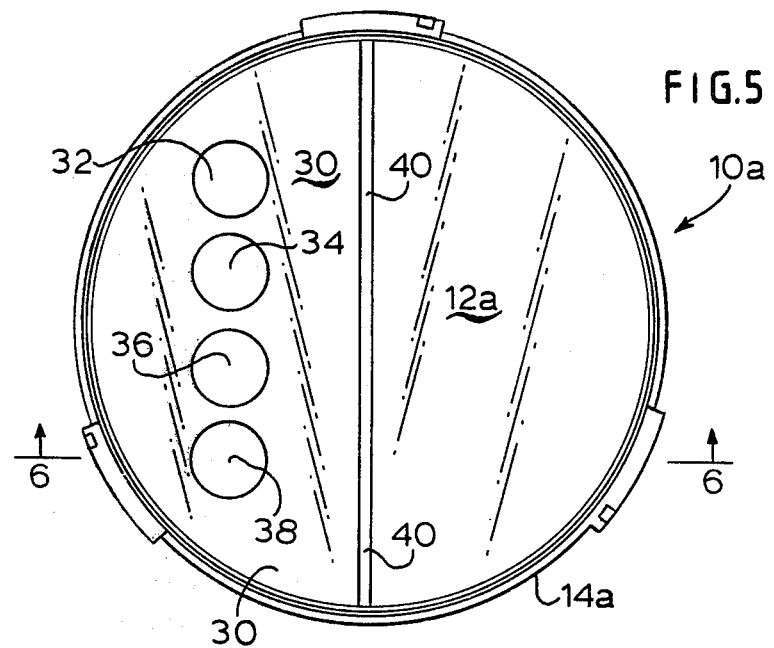
FIG. 5 is a top plan view of a bottom piece of a petri dish incorporating the system, in accordance herewith, with an arrangement of wells for receiving the reactants for the system of the invention here.
Figure 7:
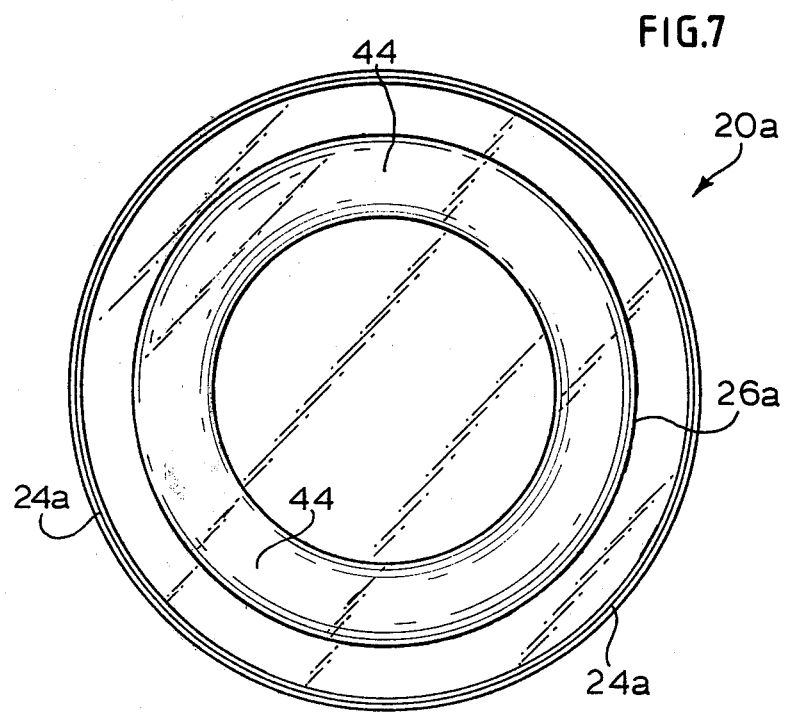
FIG. 7 is a bottom plan view of a top piece of a petri dish incorporating various aspects of the system of the invention herein.

Referring now to FIGS. 5, 6 and 7, an alternative form of the bottom piece of a petri dish is shown with a integral solid platform 30 having formed therein a plurality of space apart wells 32, 34, 36 and 38 for receiving reactants in the system, in accordance herewith. Platform 30 forms a wall 40 in petri dish bottom part 10a which defines with the opposing wall 14a an open area 46 for receiving a culture media to be maintained in petri dish 10a. Cooperating top piece 20a which forms a completed sealable petri dish with bottom piece 10a includes, in this form of petri dish a catalyst ring 44 positioned in the top as shown in FIG. 7. The catalyst may be in the form of a paintable system of palladium on an alumina support formulated in accordance with the teachings in co-pending U.S. patent application Ser. No. 26,337, filed Apr. 2, 1979, which is hereby incorporated by reference in its entirety. Alternatively, one of the wells 32, 34, 36 or 38 may hold the catalyst, and there will be no catalyst in top piece 20a. Well 32 for example, may contain the metallic couple of the invention, well 34 may contain an anaerobic indicator for indicating an anaerobic condition in the sealed container, and well 36 may contain a carbon dioxide tablet of the formation noted in U.S. application Ser. No. 26,337 noted above. Well 38, in this form of the invention, would hold the catalyst, as discussed above.

Referring again to FIGS. 1 and 2 of the invention, the dimensions of top part 20 are such that annular upstanding wall portion 50 extending at a 45° angle from wall 14 cooperates with annular wall portion 52 defined in top part 20 at a 45° angle from wall 24 for sealing engagement of top and bottom parts 10 and 20.

Thus, as will be appreciated from the foregoing, there is provided in accordance herewith, a complete system for anaerobiosis of cultures which may be controlled individually in the petri dish of the invention, and wherein the petri dish or container may be opened and inspected, and thereafter closed with a resulting automatic re-establishment of anaerobiosis. The arrangement is such that the petri dish may include various forms of catalytic systems, and may include provisions for generating carbon dioxide as required. Because of the individual nature of the anaerobic systems, in accordance herewith, and the automatic nature thereof, the system of the invention is an economically attractive package which may be produced with mass production techniques. The arrangement allows for relatively inexpensive culturing on an individual basis, which is particularly important for clinical operations, and university experimental procedures.

While the methods, compositions and apparatus herein disclosed form preferred embodiments of this invention, this invention is not limited to those specific methods, compositions or forms of apparatus and changes can be made therein without departing from the scope of this invention which is defined in the appended claims.

What is claimed is:

1. A system for producing an atmosphere for use in culturing anaerobic microorganisms, characterized by
   (a) a sealable container;
   (b) a material in said container which when contacted by water generates a gas capable of reacting with oxygen to provide an atmosphere for culturing anaerobic microorganisms;
   (c) said material being a metal-metal salt couple wherein said metal is selected from the group consisting of magnesium, beryllium, barium, strontium, and calcium and wherein said metal salt is selected from the group consisting of copper, platinum, palladium, tin, iron, nickel and cobalt; and
   (d) catalytic means in said container for catalyzing reaction between oxygen and gas generated in said container.

2. The system of claim 1, further characterized by
   (a) said metal-metal salt couple includes said catalytic means.

3. The system of claim 2, further characterized by
   (a) said metal is magnesium metal; and
   (b) said metal salt is a member selected from the group consisting of palladium, nickel, platinum and cobalt.

4. The system of claim 1, further characterized by
   (a) said metal is magnesium; and
   (b) said metal salt is a copper salt.

5. The system of claim 1, further characterized by said sealable container comprising
   (a) a bottom portion;
   (b) a plurality of wells in said bottom portion for receiving reactants in said system;
   (c) a top portion; and
   (d) cooperating locking means on said top and bottom portions.

6. The system of claim 5, further characterized by
   (a) one-half of said bottom portion is solid;
   (b) said plurality of wells formed is in said solid one half; and
   (c) the remaining half of said bottom portion opposite said solid half for receiving a media to be cultured.

7. The system of claim 5, further characterized by
   (a) said catalytic means painted onto the internal surface of said top portion.

8. The system of claim 7, further characterized by
   (a) said catalytic means is palladium supported on alumina.

9. The system of claim 1, further characterized by
   (a) a tablet for generating carbon dioxide.

10. The system of claim 9, further characterized by
    (a) said tablet is comprised of a water soluble solid carbonate and a water soluble solid acid.

11. The system of claim 9, further characterized by
(a) a carbon dioxide indicator.

12. The system of claim 1, further characterized by
(a) at least one anaerobic indicator in said container.

13. A system for use in generating an anaerobic atmosphere in a sealable container, characterized by
(a) a material which when contacted by water generates a gas capable of reacting with oxygen to provide an atmosphere for culturing anaerobic microorganisms;
(b) said material being a metal-metal salt couple wherein said metal is selected from the group consisting of magnesium, beryllium, barium, strontium, and calcium and wherein said metal salt is selected from the group consisting of copper, platinum, palladium, tin, iron, nickel and cobalt; and
(c) catalytic means for catalyzing reaction between oxygen and gas generated by said material.

14. The system of claim 13, further characterized by
(a) said material is a magnesium-copper couple.

15. The system of claim 14, further characterized by
(a) said catalytic means is a supported palladium.

16. The system of claim 14, further characterized by
(a) said material is a magnesium-palladium couple.

17. The system of claim 13, further characterized by
(a) said material is in the form of a tablet.

18. The system of claim 17, further characterized by
(a) a second tablet capable of generating carbon dioxide.

19. The system of claim 18, further characterized by
(a) said second tablet is comprised of a water soluble solid carbonate and a water soluble solid acid.

20. A system for producing an atmosphere for use in culturing anaerobic microorganisms, characterized by
(a) a sealable petri dish;
(b) a material in said petri dish which when contacted by water generates a gas capable of reacting with oxygen to provide an atmosphere for culturing anaerobic microorganisms;
(c) said material being a metal-metal salt couple in the form of a tablet wherein said metal is selected from the group consisting of magnesium, beryllium, barium, strontium, and calcium and wherein said metal salt is selected from the group consisting of copper, platinum, palladium, tin, iron, nickel and cobalt; and
(d) catalytic means in said container for catalyzing reaction between oxygen therein and gas generated in said container;
(e) an anaerobic indicator in said petri dish; and
(f) means on said petri dish for opening and resealing said petri dish repeatedly.

21. The system of claim 20, further characterized by
(a) said petri dish includes a cooperating top and bottom portion; and
(b) said opening and resealing means includes cooperating bayonet locking means on said top and bottom portions.

22. The system of claim 20, further characterized by
(a) said metal-metal salt couple is the product of the reaction between metallic magnesium and cupric chloride.

23. The system of claim 22, further characterized by
(a) said tablet includes a tris buffer and sodium chloride.

24. The system of claim 20, further characterized by
(a) said anaerobic indicator includes a member selected from the group consisting of methylene blue, indigo carmine and resazurin.

* * * * *